United States Patent [19]

Weeks

[11] Plant 4,737

[45] Jun. 9, 1981

[54] ROSE PLANT

[76] Inventor: O. L. Weeks, 4759 Philadelphia St., Chino, Calif. 91710

[21] Appl. No.: 150,632

[22] Filed: May 16, 1980

[51] Int. Cl.[3] ..... A01H 5/00

[52] U.S. Cl. ..... Plt./12

[58] Field of Search ..... Plt./12

*Primary Examiner*—Robert E. Bagwill
*Attorney, Agent, or Firm*—Vincent G. Gioia

[57] ABSTRACT

A new hybrid tea bicolor rose of cardinal red and pale pink coloring.

1 Drawing Figure

The present invention relates to a new and distinct variety of rose plant of the hybrid tea rose class, which was originated by my crossing as seed parent the rose known as "Sunrise Sunset" and an unnamed, unreleased and unpatented seedling of my creation as pollen parent.

Among the novel characteristics possessed by this new variety which distinguish it from its parents and all other varieties of which I am aware are high centered, exhibition form bicolor blooms with cardinal red upper petal surface and pale pink petal undersurface and a vigorous, free branching plant with abundant foliage. Flowers are exceptionally long lasting on the plant and as a cut flower and particularly useful in flower arranging. Asexual reproduction by budding of the new variety as performed in San Bernardino County, Calif., shows that the foregoing and other distinguishing characteristics come true to form and are established and transmitted through succeeding propagations.

The new and improved rose variety which I have developed is an unusually fine hybrid tea rose producing flowers of high centered, exhibition quality with appeal both as a garden and landscape plant and for cut flowers. The flowers are of medium petalage and its colors hold well upon aging.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "53B" is plate 53B of the Royal Horticultural Society Color Chart.

Parentage: Seedling.

*Seed parent.*—"Sunrise Sunset".

*Pollen parent.*—Unnamed, unreleased seedling.

Class: Hybrid tea.

The following observations are made of specimens grown outdoors in San Bernardino County, Calif. during the month of September.

1. FLOWER

Blooming habit: Intermittent to continuous.

A. Bud:

(1) *Size.*—Medium.

(2) *Form.*—Medium pointed, green bud has foliacious tip.

(3) *Color.*—When sepals first divide — 53B and greenish yellow.

(4) *Sepals.*—Simple, occasionally fancy, about same length as bud, slightly foliated.

(5) *Peduncle.*—Length — medium to short. Aspect — straight. Strength — erect. Color — 136C.

B. Bloom:

(1) *Size.*—Average size when fully expanded — about 4 to 4½ inches.

(2) *Borne.*—Primarily singly, sometimes in clusters.

(3) *Form.*—High centered, exhibition form, petals quill to point.

(4) *Petalage.*—Number of petals under normal conditions — about 28 to 32.

(5) *Color.*—As petals unfurl and through ⅓ to ½ open flower displays bicolor of cardinal red 53B petal upper surface and pale pink 56B, C or D undersurface. The petal undersurface contains some red washing, stronger toward or at the petal edge. The overall effect is a "red and silver reverse" bicolor. As flower matures to open bloom stage less pale pink of the petal undersurface is seen resulting in a Rose Bengal colored flower 57C and 57D.

C. Petals:

(1) *Texture.*—Moderately thick.

(2) *Appearance.*—Velvety.

(3) *Form.*—Slightly rounded, obovate.

(4) *Arrangement.*—Regularly arranged.

(5) *Petaloids in center.*—Yes.

(6) *Persistence.*—Drop off cleanly.

(7) *Fragrance.*—Slight.

(8) *Lasting quality.*—Very long lasting on plant and as cut flower.

2. REPRODUCTIVE ORGANS

A. Stamens, filaments and anthers:

(1) *Arrangement.*—Many stamens regularly arranged around pistils.

(2) *Color.*—Reddish yellow filaments, yellow anthers.

B. Pollen: Color — lemon.

C. Styles: Uneven, short, bunched.

D. Stigmas: Color — yellow.

E. Hips: Nonobserved.

3. PLANT

A. Form: Upright, tall.

B. Growth: Vigorous, free branching, heavy canes.

C. Foliage: Compound 3 to 7 leaflets.

(1) *Size.*—Medium.

(2) *Quantity.*—Abundant.

(3) *Color.*—New foliage: Purplish bronze becoming near 139C. Old foliage: Upper side — near 139A. Under side — near 191A.

(4) *Shape.*—Ovoid, acute.

(5) *Texture.*—Upper side is glossy, leathery and under side is dull.

(6) *Edge.*—Serrated.

(7) *Serration.*—Coarse.

(8) *Leaf stem.*—Color — near to 139C.

(9) *Stipules.*—Long.

(10) *Resistance to disease.*—Mildew — good. Rust — good.

D. Wood:

(1) *New wood.*—Color — near 138B. Bark — smooth, shiny.

(2) *Old wood.*—Color — near 138A. Bark — smooth, shiny.

E. Thorns:

(1) *Thorns.*—Quantity (main stalk): many. On laterals from stalk — many. Form — planted downward. Length — medium. Color — green to tan. Position — scattered.

(2) *Prickles.*—Few.

F. Winter hardiness: Good winter hardiness.

I claim:

1. A new and distinct variety of rose plant of the hybrid tea class, substantially as shown and described characterized particularly by bicolor cardinal red and pale pink coloring and high centered flowers borne primarily singly to a stem, and are attractive on the plant and as cut flowers.

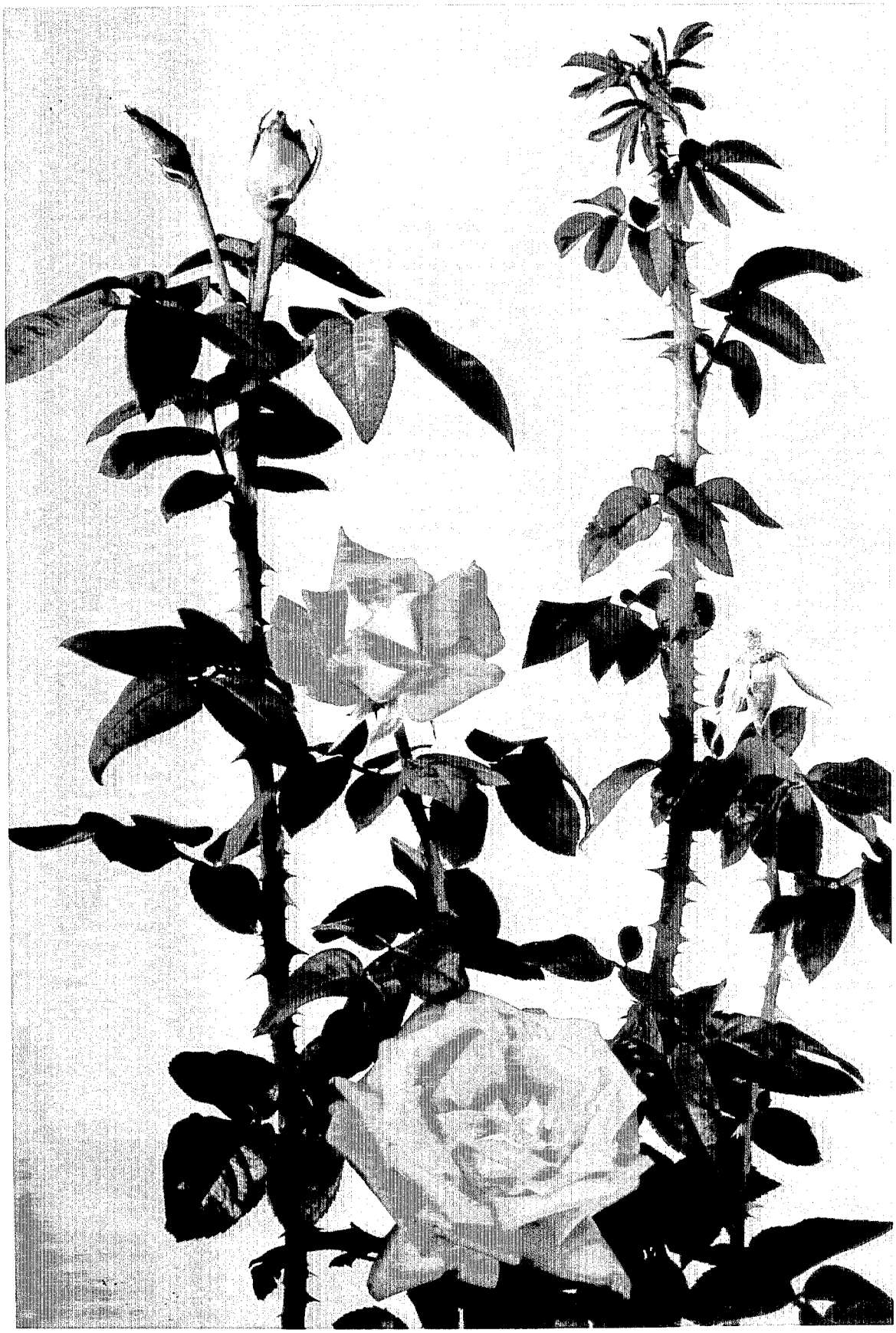

* * * * *